United States Patent
Cong et al.

(10) Patent No.: US 10,159,703 B2
(45) Date of Patent: Dec. 25, 2018

(54) TRADITIONAL CHINESE MEDICINE COMPOSITION FOR RELIEVING CHRONIC PAIN AND PREPARATION METHOD AND USE THEREOF

(71) Applicant: INFINITUS (CHINA) COMPANY LTD., Jiang Men, Guangdong (CN)

(72) Inventors: Renhuai Cong, Jiang Men (CN); Fangli Ma, Jiang Men (CN); Chung Wah Ma, Jiang Men (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 34 days.

(21) Appl. No.: 15/407,730

(22) Filed: Jan. 17, 2017

(65) Prior Publication Data

US 2017/0209508 A1  Jul. 27, 2017

(30) Foreign Application Priority Data

Jan. 27, 2016  (CN) .......................... 2016 1 0057452

(51) Int. Cl.
*A61K 36/00* (2006.01)
*A61K 36/185* (2006.01)
*A61K 36/54* (2006.01)

(52) U.S. Cl.
CPC ............ *A61K 36/185* (2013.01); *A61K 36/54* (2013.01); *A61K 2236/15* (2013.01); *A61K 2236/331* (2013.01)

(58) Field of Classification Search
CPC .................................................... A61K 36/00
See application file for complete search history.

(56) References Cited

U.S. PATENT DOCUMENTS

2004/0047930 A1* 3/2004 Webbe ................ A61K 9/0014
424/769

FOREIGN PATENT DOCUMENTS

CN  104664309 A  *  6/2015

OTHER PUBLICATIONS

Sumiwi et al, Analysis of chemical composition and its analgesic and anti-inflammatory activity of essential oil of sintoc bark (Cinnamomum sintoc bl.) using in vivo methods. Journal of Applied Pharmaceutical Science (2015), vol. 5, No. 2, pp. 58-65 (Year: 2015).*

* cited by examiner

*Primary Examiner* — Qiuwen Mi
(74) *Attorney, Agent, or Firm* — U.S. Fairsky LLP; Yue Robert Xu

(57) ABSTRACT

The present invention relates to the technical field of healthcare food, especially relates to a traditional Chinese medicine composition for relieving chronic pain and preparation method and use thereof. The traditional Chinese medicine composition includes cinnamon bark oil and nutmeg oil. The traditional Chinese medicine composition of the present invention can effectively relieve chronic pain, and the effect of the composition is superior to single agent, and cinnamon bark oil and nutmeg oil can be used pharmaceutically and bromatologically and do not have side effects.

2 Claims, No Drawings

TRADITIONAL CHINESE MEDICINE COMPOSITION FOR RELIEVING CHRONIC PAIN AND PREPARATION METHOD AND USE THEREOF

CROSS REFERENCE OF RELATED APPLICATIONS

The present application claims the priority of Chinese Patent Application No. 201610057452.2 as filed on Jan. 27, 2016 and titled with "A traditional Chinese medicine composition for relieving chronic pain and preparation method and use thereof", and the disclosure of which is incorporated herein by reference.

FIELD

The present invention relates to the technical field of health-care food, especially relates to a traditional Chinese medicine composition for relieving chronic pain and preparation method and use thereof.

BACKGROUND

Chronic pain is clinically a very common disease, which means the pain that lasts for over one month. Chronic pain is figuratively regarded as "die of cancer". Chronic pain results from Yuanshang disease. According to statistics, the incidence of chronic pain in China is about 35%-45% at present, and higher in old people, which is about 75%-90%. Chronic pain not only brings patients physical discomfort, but also indicates physical deterioration or health crisis in some parts. Because of its long persistent period and refractory characteristics, chronic pain results in functional disorder of body, decreased immunity and various complications, eventually leading to a series of psychological, behavioral, family and social problems, thereby significantly influences the life quality of patients and brings tremendous loss to society.

Chronic pain has always been occupied by analgesics, mainly Western medicine, such as ibuprofen, opioids, which are attended with good results. However, studies demonstrate that up to above 50% of the patients still can not be sufficiently relieved of pain after analgesic therapy with Western medicine. Some patients even develop psychological dependence and physical dependence in varying degrees due to long-term analgesics therapy, thereby further decreasing the life quality of patients. Meanwhile, Western medicine may result in certain side effects. For example, ibuprofen may result in side effects such as dyspepsia, rash, increase in transaminase. Time reports that, taking ibuprofen chronically may result in renal failure; taking opioids may result in side effects such as nausea, vomiting, constipation, excessive appeasement, biliary colic, uroschesis, mental derangement and neurotoxicity, respiratory depression and drug dependence. Traditional Chinese medicine attracts extensive attention from medical community due to low side effects thereof.

Cinnamon bark is the dry tree bark of the lauraceae plant cinnamon, which is listed as top grade in ancient herbal medicine. Cinnamon bark oil is the volatile oil obtained from extracting dry branches and leaves of cinnamon bark by water vapor distillation, which can be used as fragrance. Cinnamon bark contains 1%-2% volatile oil, which is a yellow or yellow brown clear liquid; and has a specific aroma of cinnamon bark, sweet and spicy taste. Exposed in air or deposited for a long time, the colour darkens and the consistency becomes dense. Cinnamon bark oil is extensively used in medicine, food and light chemical industry.

Myristica fragrans Houtt is an aiphyllium from Myristica, Myristicaceae, which is mainly produced from Indonesia, Sri Lanka, Mauritius, India, the United States, the United Kingdom, and China Sichuan and Guangxi. Nutmeg oil is obtained from extracting the seeds by water vapor distillation, with an oil yield of 6%-10%. Nutmeg oil is a liquid between achromatic color and light yellow colour, with a relative density of 30.883-30.917, a refractive index of 1.475-1.488 and thick, fresh and sweet and spicy taste. The main ingredients of nutmeg oil include nutmeg phenol ether, eugenol, isoeugenol, linalool, geraniol, safrole, camphol, limonene, pinene and so on.

Currently, there is no report concerning the combined use of cinnamon bark oil and nutmeg oil, let alone any reports the synergistic effect obtained in relieving pain after combined use.

SUMMARY

The present invention provides a traditional Chinese medicine composition for relieving chronic pain and preparation method and use thereof. The traditional Chinese medicine composition can effectively relieve chronic pain, and the effect of composition is superior to the single, which have synergistic effect.

To achieve the above invention purpose, the present invention provides the following technical solutions:

The present invention provides a traditional Chinese medicine composition consist of cinnamon bark oil and nutmeg oil.

The study found that, the composition of cinnamon bark oil and nutmeg oil can significantly inhibit the inflammation caused by xylene, significantly reduce writhing times of mice, can significantly reduce the swelling degree in rats, significantly reduce pain threshold of rats, reduce the content of pain related factors. The results demonstrate that the traditional Chinese medicine composition in the present invention can effectively relieve chronic pain, and the effect of composition is superior to the effect of single drug, i.e. the two have synergistic effect.

In some examples provided by the present invention, cinnamon bark oil is obtained from cinnamon bark by water vapor distillation.

In some examples provided by the present invention, nutmeg oil is obtained from nutmeg by water vapor distillation.

As a preferred selection, the mass ratio of cinnamon bark oil to nutmeg oil is (1-99):(1-99).

Preferably, the mass ratio of cinnamon bark oil to nutmeg oil is (1-40): (1-40).

Preferably, the mass ratio of cinnamon bark oil to nutmeg oil is (1-20):(1-20).

Preferably, the mass ratio of cinnamon bark oil to nutmeg oil is (1-10):(1-20).

Preferably, the mass ratio of cinnamon bark oil to nutmeg oil is (1-10):(1-10).

More preferably, the mass ratio of cinnamon bark oil to nutmeg oil is (1-5):(1-4).

In some examples provided by the present invention, the mass ratio of cinnamon bark oil to nutmeg oil is 20:1.

In some examples provided by the present invention, the mass ratio of cinnamon bark oil to nutmeg oil is 10:1.

In other examples provided by the present invention, the mass ratio of cinnamon bark oil to nutmeg oil is 5:1.

In other examples provided by the present invention, the mass ratio of cinnamon bark oil to nutmeg oil is 1:1.

In other examples provided by the present invention, the mass ratio of cinnamon bark oil to nutmeg oil is 1:4.

In other examples provided by the present invention, the mass ratio of cinnamon bark oil to nutmeg oil is 1:10.

In other examples provided by the present invention, the mass ratio of cinnamon bark oil to nutmeg oil is 1:20.

The present invention further provides a preparation method of the traditional Chinese medicine composition, including the following steps:

Subjecting cinnamon bark to water vapor distillation for the first extraction, yielding cinnamon bark oil;

Subjecting nutmeg to water vapor distillation for the second extraction, yielding nutmeg oil;

Mixing cinnamon bark oil and nutmeg oil, yielding traditional Chinese medicine composition.

As a preferred selection, the mass ratio of cinnamon bark oil to nutmeg oil is (1-99):(1-99).

Preferably, the mass ratio of cinnamon bark oil to nutmeg oil is (1-40):(1-40).

Preferably, the mass ratio of cinnamon bark oil to nutmeg oil is (1-20):(1-20).

Preferably, the mass ratio of cinnamon bark oil to nutmeg oil is (1-10):(1-20).

Preferably, the mass ratio of cinnamon bark oil to nutmeg oil is (1-10):(1-10).

More preferably, the mass ratio of cinnamon bark oil to nutmeg oil is (1-5):(1-4).

In some examples provided by the invention, the mass ratio of cinnamon bark oil to nutmeg oil is 20:1.

In some examples provided by the invention, the mass ratio of cinnamon bark oil to nutmeg oil is 10:1.

In other examples provided by the invention, the mass ratio of cinnamon bark oil to nutmeg oil is 5:1.

In other examples provided by the invention, the mass ratio of cinnamon bark oil to nutmeg oil is 1:1.

In other examples provided by the invention, the mass ratio of cinnamon bark oil to nutmeg oil is 1:4.

In other examples provided by the invention, the mass ratio of cinnamon bark oil to nutmeg oil is 1:10.

In other examples provided by the invention, the mass ratio of cinnamon bark oil to nutmeg oil is 1:20.

As a preferred selection, the first extraction is: pulverizating cinnamon bark and soaking it into water, then extracting by distillation under heat; the time for extraction by distillation is 0.5-6 h.

Preferably, the time for extraction by distillation of cinnamon bark is 1-6 h.

More preferably, the time for extraction by distillation of cinnamon bark is 2-4 h.

In some examples provided by the present invention, the time for extraction by distillation of cinnamon bark is 3 h.

As a preferred selection, calculated by g/mL, the ratio of cinnamon bark to water is 1:(1-40).

Preferably, calculated by g/mL, the ratio of cinnamon bark to water is 1:(1-30).

Preferably, calculated by g/mL, the ratio of cinnamon bark to water is 1:(15-25).

In some examples provided by the present invention, calculated by g/mL, the ratio of cinnamon bark to water is 1:20.

As a preferred selection, the second extraction is: pulverizating nutmeg and then soaking it into water, then extracting by Steam Distillation Method; the time for extraction is 1-12 h.

Preferably, the time for extraction by distillation of nutmeg is 3-9 h.

More preferably, the time for extraction by distillation of nutmeg is 5-7 h.

In some examples provided by the present invention, the time for extraction by distillation of nutmeg is 6 h.

As a preferred selection, calculated by g/mL, the ratio of nutmeg to water is 1:(1-20).

Preferably, calculated by g/mL, the ratio of nutmeg to water is 1:(5-15).

More preferably, calculated by g/mL, the ratio of nutmeg to water is 1:(8-12).

In some examples provided by the invention, calculated by g/mL, the ratio of nutmeg to water is 1:10.

In some examples provided by the invention, the preparation method for the traditional Chinese medicine composition includes the following steps:

After pulverizing cinnamon bark, mixing cinnamon bark powder and water, then distillating for 3 h, yielding cinnamon bark oil;

After pulverizing nutmeg, mixing nutmeg powder and water, then distillating for 6 h, yielding nutmeg oil.

Mixing cinnamon bark oil and nutmeg oil, yielding the traditional Chinese medicine composition of the present invention.

The present invention further provides a use of the traditional Chinese medicine composition in the preparation of a medicament or health-care food for relieving chronic pain; the traditional Chinese medicine composition including cinnamon bark oil and nutmeg oil; as a preferred selection, the mass ratio of cinnamon bark oil to nutmeg oil is (1-99):(1-99); preferably, the mass ratio of cinnamon bark oil to nutmeg oil is (1-40):(1-40); as a preferred selection, the mass ratio of cinnamon bark oil to nutmeg oil is (1-20):(1-20); preferably, the mass ratio of cinnamon bark oil to nutmeg oil is (1-10):(1-20); preferably, the mass ratio of cinnamon bark oil to nutmeg oil is (1-10):(1-10); more preferably, the mass ratio of cinnamon bark oil to nutmeg oil is (1-5):(1-4). In some examples provided by the present invention, the mass ratio of cinnamon bark oil to nutmeg oil is 20:1; in some examples provided by the present invention, the mass ratio of cinnamon bark oil to nutmeg oil is 10:1; in other examples provided by the present invention, the mass ratio of cinnamon bark oil to nutmeg oil is 5:1; in other examples provided by the present invention, the mass ratio of cinnamon bark oil to nutmeg oil is 1:1; in other examples provided by the present invention, the mass ratio of cinnamon bark oil to nutmeg oil is 1:4; in other examples provided by the present invention, the mass ratio of cinnamon bark oil to nutmeg oil is 1:10; in other examples provided by the present invention, the mass ratio of cinnamon bark oil to nutmeg oil is 1:20.

The present invention further provides a medicament for relieving chronic pain, including the traditional Chinese medicine composition of the present invention; the traditional Chinese medicine composition includes cinnamon bark oil and nutmeg oil; as a preferred selection, the mass ratio of cinnamon bark oil to nutmeg oil is (1-99):(1-99); preferably, the mass ratio of cinnamon bark oil to nutmeg oil is (1-40):(1-40); preferably, the mass ratio of cinnamon bark oil to nutmeg oil is (1-20):(1-20); preferably, the mass ratio of cinnamon bark oil to nutmeg oil is (1-10):(1-20); preferably, the mass ratio of cinnamon bark oil to nutmeg oil is (1-10):(1-10); more preferably, the mass ratio of cinnamon bark oil to nutmeg oil is (1-5):(1-4). In some examples provided by the present invention, the mass ratio of cinnamon bark oil to nutmeg oil is 20:1; in some examples provided by the present invention, the mass ratio of cinnamon bark oil to nutmeg oil is 10:1; in other examples provided by the present invention, the mass ratio of cinnamon bark oil to nutmeg oil is 5:1; in other examples provided by the present invention, the mass ratio of cinnamon bark oil to nutmeg oil is 1:1; in other examples provided by the present invention, the mass ratio of cinnamon bark oil to nutmeg oil is 1:4; in other examples provided by the present invention, the mass ratio of cinnamon bark oil to nutmeg oil is 1:10; in other examples provided by the present invention, the mass ratio of cinnamon bark oil to nutmeg oil is 1:20.

As a preferred selection, the medicament for relieving chronic pain of the present invention further comprises pharmaceutically acceptable excipients.

As a preferred selection, the dosage forms of the medicament for relieving chronic pain of the present invention are granules, capsules, oral liquid or syrups. However, dosage forms of the medicament are not limited thereto. Dosage forms regarded as feasible by technical personnel in the area are all within the protection scope of the present invention.

The present invention further provides a health-care food for relieving chronic pain, which includes the traditional Chinese medicine composition of the present invention; the traditional Chinese medicine composition includes cinnamon bark oil and nutmeg oil; as a preferred selection, the mass ratio of cinnamon bark oil to nutmeg oil is (1-99):(1-99); preferably, the mass ratio of cinnamon bark oil to nutmeg oil is (1-40):(1-40); preferably, the mass ratio of cinnamon bark oil to nutmeg oil is (1-20):(1-20); preferably, the mass ratio of cinnamon bark oil to nutmeg oil is (1-10):(1-20); preferably, the mass ratio of cinnamon bark oil to nutmeg oil is (1-10):(1-10); more preferably, the mass ratio of cinnamon bark oil to nutmeg oil is (1-5):(1-4). In some examples provided by the present invention, the mass ratio of cinnamon bark oil to nutmeg oil is 20:1; in some examples provided by the present invention, the mass ratio of cinnamon bark oil to nutmeg oil is 10:1; in other examples provided by the present invention, the mass ratio of cinnamon bark oil to nutmeg oil is 5:1; in other examples provided by the present invention, the mass ratio of cinnamon bark oil to nutmeg oil is 1:1; in other examples provided by the present invention, the mass ratio of cinnamon bark oil to nutmeg oil is 1:4; in other examples provided by the present invention, the mass ratio of cinnamon bark oil to nutmeg oil is 1:10; in other examples provided by the present invention, the mass ratio of cinnamon bark oil to nutmeg oil is 1:20.

As a preferred selection, the health-care food for relieving chronic pain of the present invention further comprises bromatologically acceptable excipients.

As a preferred selection, the dosage forms of the health-care food for relieving chronic pain of the present invention are granules, capsules, syrups, tablets, powder, soft candy, emulsion or oral liquid.

The present invention provides a traditional Chinese medicine composition for relieving chronic pain and preparation method and use thereof. The traditional Chinese medicine composition includes cinnamon bark oil and nutmeg oil. The present invention at least has one of the following advantages:

1. The study of the present invention found that, the combined use of cinnamon bark oil and nutmeg oil has strong inhibitory effect on the inflammation caused by xylene, significantly reduce writhing times of mice, significantly reduce the swelling degree of sole of foot of rats, significantly reduce pain threshold of rats, reduces the content of pain related factors. Test results demonstrate that the traditional Chinese medicine composition of the present invention can effectively relieve chronic pain, and the effect of composition is superior to the effect of single drug;

2. The cinnamon bark oil and nutmeg oil in the present invention can be used pharmaceutically and bromatologically and do not have side effects;

3. The preparation method of the traditional Chinese medicine composition provided by the present invention is simple and scientific, and adequately retain the oily effective ingredients of cinnamon bark and nutmeg.

DETAILED DESCRIPTION

The present invention discloses a traditional Chinese medicine composition for relieving chronic pain and preparation method and use thereof, and technical personnel in the area can realize it through suitably modifying the technological parameters by referring the contents herein. It should be especially noted that, all of the similar replacements and modifications are obvious to technical personnel in the area, which are regarded as being included in the present invention. The method and use of the present invention have been illustrated by way of the preferred Examples, and related person can obviously modify or suitably change or combine the method and use herein to realize and use the technologies of the present invention without departing from the contents, spirits and scopes of the present invention.

The crude drugs or excipients of the traditional Chinese medicine composition for relieving chronic pain and preparation method and use thereof provided by the present invention are all available in markets.

The present invention is further illustrated by combining the Examples hereinafter:

Example 1 Preparation of Traditional Chinese Medicine Composition

After pulverizing cinnamon bark, water was added at the ratio of cinnamon bark powder and water of 1 g:20 mL, then the mixture was placed into an apparatus for water vapor distillation, and was distilled under heat until the distilled water does not contain oil drips (a distillation time of 3 h), yielding cinnamon bark oil.

After pulverizing nutmeg, water was added at the ratio of nutmeg powder and water of 1 g:10 mL, then the mixture was placed into an apparatus for water vapor distillation, and was distilled under heat until the distilled water does not contain oil drips (a distillation time of 6 h), yielding nutmeg oil.

20 weight parts of cinnamon bark oil and 1 weight part of nutmeg oil were mixed, yielding a composition for relieving chronic pain.

Example 2 Preparation of Traditional Chinese Medicine Composition 10 weight parts of cinnamon bark oil obtained in Example 1 and 1 weight part of nutmeg oil obtained in Example 1 were mixed, yielding a composition for relieving chronic pain.

Example 3 Preparation of Traditional Chinese Medicine Composition 5 weight parts of cinnamon bark oil obtained in Example 1 and 1 weight part of nutmeg oil obtained in Example 1 were mixed, yielding a composition for relieving chronic pain.

Example 4 Preparation of Traditional Chinese Medicine Composition 1 weight part of cinnamon bark oil obtained in Example 1 and 1 weight part of nutmeg oil obtained in Example 1 were mixed, yielding a composition for relieving chronic pain.

Example 5 Preparation of Traditional Chinese Medicine Composition 1 weight part of cinnamon bark oil obtained in Example 1 and 4 weight parts of nutmeg oil obtained in Example 1 were mixed, yielding a composition for relieving chronic pain.

Example 6 Preparation of Traditional Chinese Medicine Composition 1 weight part of cinnamon bark oil obtained in Example 1 and 10 weight parts of nutmeg oil obtained in Example 1 were mixed, yielding a composition for relieving chronic pain.

Example 7 Preparation of Traditional Chinese Medicine Composition 1 weight part of cinnamon bark oil obtained in Example 1 and 20 weight parts of nutmeg oil obtained in Example 1 were mixed, yielding a composition for relieving chronic pain.

Example 8 Potency Experiment of the Traditional Chinese Medicine Composition Having the Function of Relieving Chronic Pain 1. Experimental Materials
1.1 Drugs and Main Agents
(1) Main Agents
The following agents were adopted: the traditional Chinese medicine composition obtained by the method of the above Example 5; complete Freund's adjuvant, SIGMA ALDRICH Corporation; polysorbate 80, Hubei Shengtian Hengchuang Biotechnology Co. Ltd.; xylene, Xi'an Shanchuan Chemical Industry Co., Ltd.; glacial acetic acid (99.5%), Tianjin Yongsheng Fine Chemical Co., Ltd.
(2) Experimental Animals
Kunming mice, SPF grade, weighting (20±2) g, provided by Animal experimental center of Hubei University of Chinese Medicine.
SD rats, male, SPF grade, weighting (150±20) g, provided by Animal experimental center of Hubei University of Chinese Medicine.
(3) Main Equipment
Electronic analytical balance, BS124S, Sartorius Stedim Corporation, Germany; Plethysmometer (Paw volume) meter, PV-200, Chengdu taimeng Technology Co., Ltd.; ELISA reader: Bio-Rad Corporation, USA; Ultra-low Temperature Freezer, Thermo Fisher Scientific, USA; Ultra-pure water system, Mill-QII, Milipore, Bedford, Mass., USA; ELISA kit, Nanjing Jiancheng Bioengineering Institute.

2. Test Method
2.1 Inflammation Model Caused by Xylene:
Kunming mice were selected and randomized into the following groups based on body weight (15 mice/group): model group, high dose sample group, middle dose sample group, low dose sample group of Example 5, single cinnamon bark oil group and single nutmeg oil group, the administration doses of Example 5 sample groups were 26.0 mg/kg, 13.0 mg/kg, 6.5 mg/kg, respectively; the administration doses of single cinnamon bark oil group and single nutmeg oil group were both 13.0 mg/kg. Intragastric administration was performed, once per day, for consecutive 14 days. Meanwhile, model group was intragastrically administrated with equal volume of distilled water. In 30 min after the last administration, right ears of the mice were coated with xylene (two sides) for modelling, and the left ears were served as control. The mice were sacrificed by cervical dislocation, and ear sheets were taken at the symmetrical parts of the left and right ears. Inhibition rates were calculated, and the recovery effects of the test substance on inflammation models were observed.

Swelling degree=mass of the right ear−mass of the left ear;

Swelling rate=[(mass of the right ear−mass of the left ear)/mass of the left ear]×100%

2.2 Pain Model Induced by Acetic Acid Writhing:
Kunming mice were selected and randomized into the following groups based on body weight (15 mice/group): model group, high dose sample group, middle dose sample group, low dose sample group of Example 5, single cinnamon bark oil group and single nutmeg oil group, the administration doses of Example 5 sample were 26.0 mg/kg, 13.0 mg/kg, 6.5 mg/kg, respectively; the administration doses of single cinnamon bark oil group and single nutmeg oil group were both 13.0 mg/kg. Intragastric administration was performed, once per day, for consecutive 14 days. Meanwhile, model group was intragastrically administrated with equal volume of distilled water. In 30 min after the last administration, acetic acid solution was administered by intraperitoneal injection for modeling, and writhing responses were observed. Analgesic rates were calculated, and the recovery effects of the composition on pain model were observed.

2.3. Arthritis Model Induced by Freund's Adjuvant:
Male SD rats were randomized into the following groups based on body weight (15 rats/group): blank group, model group, high dose sample group, middle dose sample group, low dose sample group of Example 5, the administration doses of Example 5 sample were 18.0 mg/kg, 9.0 mg/kg, 4.5 mg/kg, respectively; the administration doses of single cinnamon bark oil group and single nutmeg oil group were both 9.0 mg/kg. ImmediatBefore using, the samples of each group were dissolved in polysorbate 80, and suspensions were formulated according to an administration volume of 1 mL/100 g, and were administered intragastrically. The volumes (mL) of voix pedis below ankle joint of right posterior paw of the rats of each of the groups were determined using water drainage method. In 3 days before inflammation induction, the samples were administered intragastrically according to corresponding administration doses, once per day, for consecutive 3 days. Afterwards, rats of each group were administered with 0.1 mL of complete Freund's adjuvant by intradermal injection at the toes of right posterior paw for inflammation induction. The volumes (mL) of voix pedis below ankle joint of right posterior paw of the rats (before inflammation induction and 3 h, 6 h, 24 h after inflammation induction) were determined using water drainage method. The determination was performed for 3 times and the average values was obtained. After inflammation induction, for each group, intragastric administration was continued, once per day, and the volume of the foot, which was not subjected to inflammation induction, was determined to observe the secondary swelling of voix pedis of the rats.

After the experiment, blood was extracted from eye sockets, collected into EP tubes added with EDTA and Aprotinin beforehand. The blood was homogenized and left stand. plasma was separated to determine the content of P substance in blood. The rats were sacrificed, and the skin tissues on footplate of left and right feet were cut and fixed with 10% formalin. The slices of paraffin blocks of paraffin-embedded skin tissues were respectively subjected to NK-1R and COX-2 immunohistochemistry staining and were examined under microscope.

The results were indicated by means of mean±SD. The results were subjected to ANOVA analysis using SPSS statistical software (12.0).

3. Experimental Results

After the experiments, the indicator levels of the rats in each groups were shown in Table 1-Table 4.

TABLE 1

The effect in each mice groups on ear swelling degree, inhibition rate

| Groups | The number of cases | Ear swelling degree (mg) | Inhibition rate (%) |
|---|---|---|---|
| model group | 15 | $12.2 \pm 3.4^{\#}$ | — |
| high dose group | 15 | $4.8 \pm 2.0^{×}$ | 62.7 |
| middle dose group | 15 | $5.3 \pm 4.1^{×}$ | 59.6 |
| low dose group | 15 | $6.9 \pm 1.5^{×}$ | 47.3 |
| single cinnamon bark oil group | 15 | $7.7 \pm 4.1$ | 38.7 |
| single nutmeg oil group | 15 | $9.0 \pm 2.7$ | 31.3 |

Note:
$^{\#}$compared with blank group, $p < 0.05$,
$^{\#\#}$compared with blank group, $p < 0.01$,
$^{×}$compared with model group, $p < 0.05$,
$^{××}$compared with model group, $p < 0.05$.

The above experimental results show that, after coating the left ear of mice with xylene, compared with the right ear, the left ear appear obvious swelling, and there was significant difference (p<0.05) between model group and blank group, suggesting that ear swelling model by xylene was successful; there was statistical significance (p<0.05) when comparing high, middle, low dose groups with model group, suggesting that the traditional Chinese medicine composition of Example 5 in high, middle, low dose groups have a strong inhibitory effect on inflammation caused by xylene, which are better than single.

TABLE 2 writhing times, analgesic rates of mice

| Groups | The number of cases | Writhing times | Analgesic rate (%) |
|---|---|---|---|
| model group | 15 | $24.60 \pm 11.28$ | — |
| high dose group | 15 | $11.00 \pm 5.19^{×}$ | 71.13 |
| middle dose group | 15 | $11.04 \pm 4.47^{×}$ | 69.60 |
| low dose group | 15 | $13.68 \pm 11.61^{×}$ | 55.38 |
| single cinnamon bark oil group | 15 | $13.60 \pm 7.83$ | 54.73 |
| single nutmeg oil group | 15 | $12.88 \pm 6.57^{×}$ | 60.80 |

Note:
$^{\#}$compared with blank group, $p < 0.05$,
$^{\#\#}$compared with blank group, $p < 0.01$,
$^{×}$compared with model group, $p < 0.05$,
$^{××}$compared with model group, $p < 0.05$.

According the above experimental results, after intraperitoneal injection of acetic acid, observe the writhing time and calculate the analgesic rate: compared with blank group, writhing time in model group, were significantly increased, statistical significance (p<0.05); There were significant difference (P<0.05) between the model group and any other dose groups, in which the writhing time were reduced, significant difference. It is demonstrated that high, middle, low dose groups of the traditional Chinese medicine composition of Example 5 can significantly reduce the writhing time of mice, and the effect was superior than single agent.

TABLE 3

The foot swelling degree of paw in rats of each group

| Groups | The number of cases | Swelling degree 3 h | Swelling degree 6 h | Swelling degree 24 h | Swelling degree 7 d | Swelling degree 9 d | Swelling degree 11 d |
|---|---|---|---|---|---|---|---|
| blank group | 15 | $1.61 \pm 0.14$ | $1.62 \pm 0.15$ | $1.61 \pm 0.14$ | $1.63 \pm 0.14$ | $1.61 \pm 0.15$ | $1.61 \pm 0.14$ |
| model group | 15 | $2.20 \pm 0.12^{\#}$ | $2.26 \pm 0.19^{\#}$ | $2.21 \pm 0.11^{\#}$ | $2.08 \pm 0.15^{\#}$ | $2.22 \pm 0.10^{\#}$ | $2.13 \pm 0.13^{\#}$ |
| high dose group | 15 | $1.82 \pm 0.17^{×}$ | $2.01 \pm 0.28^{×}$ | $1.93 \pm 0.21$ | $2.11 \pm 0.35$ | $1.10 \pm 0.21^{×}$ | $1.90 \pm 0.15$ |
| middle dose group | 15 | $2.01 \pm 0.17^{×}$ | $2.02 \pm 0.18$ | $2.10 \pm 0.25$ | $1.99 \pm 0.29$ | $1.91 \pm 0.25^{×}$ | $2.08 \pm 0.13^{×}$ |
| low dose group | 15 | $2.12 \pm 0.17$ | $2.33 \pm 0.13$ | $2.28 \pm 0.18$ | $2.06 \pm 0.13$ | $2.21 \pm 0.18$ | $2.11 \pm 0.14$ |
| single cinnamon bark oil group | 15 | $1.80 \pm 0.11^{×}$ | $1.11 \pm 0.11^{×}$ | $2.16 \pm 0.19$ | $2.17 \pm 0.12$ | $2.11 \pm 0.08^{×}$ | $2.05 \pm 0.05$ |
| single nutmeg oil group | 15 | $2.33 \pm 0.12$ | $2.30 \pm 0.06$ | $2.27 \pm 0.14$ | $2.15 \pm 0.18$ | $2.18 \pm 0.12$ | $2.10 \pm 0.11$ |

Note:
$^{\#}$compared with blank group, $p < 0.05$,
compared with blank group, $p < 0.01$,
$^{×}$compared with model group, $p < 0.05$,
×·× compared with model group, $p < 0.01$.

The above experimental results show that, the swelling degree in model group was higher than in blank group (P<0.05); compared with the model group, there was significant difference in higher dose group (P<0.05) and in middle dose group (P<0.05) at 3 h, 11 d. It is demonstrated that high and middle dose groups of Example 5 can significantly reduce the swelling degree, and the effect thereof is superior to single agent.

Comparison between the pain related factors NK-1R, COX-2 in each group: compared with blank group, model group has significant difference (P<0.05), compared with model group, each of the dose groups has significance (P<0.05).

It is demonstrated that high, middle, low dose groups of the traditional Chinese medicine composition of Example 5

TABLE 4

Thermalgia threshold of rats

| Groups | The number of cases | Pain threshold 3 h | Pain threshold 6 h | Pain threshold 24 h | Pain threshold 7 d | Pain threshold 9 d | Pain threshold 11 d |
|---|---|---|---|---|---|---|---|
| blank group | 15 | 15.44 ± 2.2 | 14.87 ± 1.35 | 15.43 ± 2.6 | 14.85 ± 3.61 | 15.84 ± 3.33 | 14.17 ± 3.53 |
| model group | 15 | 15.56 ± 3.42 | 18.81 ± 2.38$^{\#}$ | 16.68 ± 2.21$^{\#}$ | 17.79 ± 1.83$^{\#}$ | 16.12 ± 3.13$^{\#}$ | 16.80 ± 4.13$^{\#}$ |
| high dose group | 15 | 12.22 ± 3.21$^{✕}$ | 14.41 ± 2.33$^{✕}$ | 14.40 ± 2.89$^{✕}$ | 12.13 ± 3.29$^{✕}$ | 13.13 ± 2.14$^{✕}$ | 12.71 ± 1.87$^{✕}$ |
| middle dose group | 15 | 15.09 ± 5.17$^{✕}$ | 14.63 ± 5.28$^{✕}$ | 14.63 ± 5.28$^{✕}$ | 12.27 ± 3.12$^{✕}$ | 12.87 ± 3.16$^{✕}$ | 13.08 ± 2.15$^{✕}$ |
| low dose group | 15 | 15.02 ± 2.17$^{✕}$ | 15.02 ± 0.18$^{✕}$ | 15.02 ± 0.18$^{✕}$ | 16.16 ± 2.35 | 15.91 ± 3.21 | 16.90 ± 3.21 |
| single cinnamon bak oil group | 15 | 15.06 ± 4.77$^{✕}$ | 16.34 ± 3.18$^{✕}$ | 16.24 ± 3.18$^{✕}$ | 17.11 ± 1.13$^{✕}$ | 13.33 ± 3.08$^{✕}$ | 16.05 ± 3.05$^{✕}$ |
| single nutmeg oil group | 15 | 16.33 ± 2.12 | 16.50 ± 3.06$^{✕}$ | 16.37 ± 2.14$^{✕}$ | 15.25 ± 3.18 | 16.18 ± 4.12 | 15.11 ± 1.09 |

Note:
$^{\#}$compared with blank group, p < 0.05,
compared with blank group, p < 0.01,
$^{✕}$compared with model group, p < 0.05,
✕·✕ compared with model group, p < 0.01.

According the above experimental results, compared with blank group, pain threshold of rats in model group all have significant difference (P<0.05) at 3 h, 6 h, 24 h, 7 d, 9 d, 11 d; compared with model group, high, middle dose groups all have significant difference (P<0.05), compared with model group, low dose group has significant difference (P<0.05) at 3 h, 6 h. It is demonstrated that high, middle dose groups in Example 5 can significantly reduce pain threshold of rats, and the effects are superior to single agent.

can significantly reduce the content of pain related factors, and the effects thereof are superior to single agent.

4. Summary of Experiments

Summarizing from the interference effects of each group on inflammation model caused by xylene, pain model induced by acetic acid writhing and arthritis model induced by Freund's adjuvant, each of the dose groups has certain therapeutic effects on relieving chronic pain. The therapeutic effects in high, middle dose groups are relatively significant in relieving chronic pain. Nevertheless, the content changes

TABLE 5

Content of pain related factors NK-1R, COX-2 in different groups

| Groups | The number of cases | Content of P substance (pg/mL) | NK-1R | COX-2 |
|---|---|---|---|---|
| blank group | 15 | 178.913 ± 22.694 | 0.0222 ± 0.00073 | 0.0146 ± 0.001 |
| model group | 15 | 458.778 ± 114.340$^{\#}$ | 0.0648 ± 0.00782$^{\#}$ | 0.0384 ± 0.00248$^{\#}$ |
| high dose group | 15 | 216.928 ± 31.274$^{✕}$ | 0.0298 ± 0.00187$^{✕}$ | 0.0165 ± 0.00123$^{✕}$ |
| middle dose group | 15 | 279.858 ± 6.324$^{✕}$ | 0.0383 ± 0.00084$^{✕}$ | 0.0215 ± 0.00382$^{✕}$ |
| low dose group | 15 | 311.570 ± 19.544 | 0.0405 ± 0.00065$^{✕}$ | 0.0253 ± 0.00182$^{✕}$ |
| single cinnamon bark oil group | 15 | 266.654 ± 17.547$^{✕}$ | 0.0393 ± 0.00483$^{✕}$ | 0.0245 ± 0.00184$^{✕}$ |
| single nutmeg oil group | 15 | 350.840 ± 99.966 | 0.0455 ± 0.00125$^{✕}$ | 0.0299 ± 0.00052$^{✕}$ |

Note:
$^{\#}$compared with blank group, p < 0.05,
$^{\#\#}$compared with blank group, p < 0.01,
$^{✕}$compared with model group, p < 0.05,
✕·✕compared with model group, p < 0.01.

According the above experimental results, content of P substance in each group are compared as follows, compared with blank group, model group has significant difference (P<0.05), compared with model group, each dose group has significant difference (P<0.05).

of P substance and the pain related inflammatory factors in arthritis model induced by Freund's adjuvant, and the determined results of pain related inflammatory factors support the results.

Example 9 Experiment Studies of the Traditional Chinese Medicine Composition in Relieving Chronic Pain Referring to the experiment methods of Example 8, the compositions of Examples 1-4 and Examples 6, 7 replace the composition of Example 5.

The administration dose for mice in sample groups was 13.0 mg/kg·d; the administration dose for rats was 9.0 mg/kg·d.

The change levels of biochemical indicators of rats of each group were shown in Tables 6-10.

TABLE 6

The effect in each groups on ear swelling degree, inhibition rate

| Groups | The number of cases | Ear swelling degree (mg) | Inhibition rate (%) |
|---|---|---|---|
| model group | 15 | 12.2 ± 3.4[#] | — |
| Example 1 | 15 | 8.0 ± 1.2 | 35.8 |
| Example 2 | 15 | 7.6 ± 2.4 | 40.1 |
| Example 3 | 15 | 6.7 ± 3.4[✕] | 48.8 |
| Example 4 | 15 | 6.3 ± 1.2[✕] | 54.6 |

TABLE 6-continued

The effect in each groups on ear swelling degree, inhibition rate

| Groups | The number of cases | Ear swelling degree (mg) | Inhibition rate (%) |
|---|---|---|---|
| Example 6 | 15 | 7.9 ± 3.1 | 35.4 |
| Example 7 | 15 | 8.9 ± 2.1[✕] | 31.0 |

Note:
[#]compared with blank group, $p < 0.05$,
[##]compared with blank group, $p < 0.01$,
[✕]compared with model group, $p < 0.05$,
[✕✕]compared with model group, $p < 0.01$.

TABLE 7 writhing times, analgesic rate of mice

| Groups | The number of cases | Writhing times | Analgesic rate (%) |
|---|---|---|---|
| model group | 15 | 24.60 ± 11.28 | — |
| Example 1 | 15 | 12.96 ± 4.83[✕] | 59.98 |
| Example 2 | 15 | 13.01 ± 4.33[✕] | 56.12 |
| Example 3 | 15 | 12.11 ± 6.67[✕] | 65.07 |
| Example 4 | 15 | 11.99 ± 5.88[✕] | 66.56 |
| Example 6 | 15 | 12.46 ± 7.83 | 61.10 |
| Example 7 | 15 | 11.52 ± 4.53[✕] | 69.63 |

Note:
[#]compared with blank group, $p < 0.05$,
[##]compared with blank group, $p < 0.01$,
[✕]compared with model group, $p < 0.05$,
[✕✕]compared with model group, $p < 0.05$.

TABLE 8

The foot swelling degree of paw in rats of each group

| Groups | The number of cases | Swelling degree 3 h | Swelling degree 6 h | Swelling degree 24 h | Swelling degree 7 d | Swelling degree 9 d | Swelling degree 11 d |
|---|---|---|---|---|---|---|---|
| blank group | 15 | 1.61 ± 0.14 | 1.62 ± 0.2 | 1.61 ± 0.14 | 1.63 ± 0.14 | 1.61 ± 0.15 | 1.61 ± 0.14 |
| model group | 15 | 2.20 ± 0.12[#] | 2.26 ± 0.2[#] | 2.21 ± 0.11[#] | 2.11 ± 0.15[#] | 2.22 ± 0.10[#] | 2.13 ± 0.13[#] |
| Example | 15 | 2.10 ± 0.17 | 2.12 ± 0.18 | 2.11 ± 0.17[✕] | 2.06 ± 0.13 | 2.06± | 2.05 ± 0.15[✕] |
| Example | 15 | 2.16 ± 0.22 | 2.22 ± 0.24 | 2.28 ± 0.22 | 2.15 ± 0.12 | 1.99± | 2.01 ± 0.11[✕] |
| Example | 15 | 2.00 ± 0.10 | 2.12 ± 0.16 | 2.11 ± 0.17 | 1.97 ± 0.18 | 2.03± | 1.98 ± 0.26[✕] |
| Example | 15 | 1.81 ± 0.12[✕] | 2.09 ± 0.26 | 2.16 ± 0.33 | 1.98 ± 0.09 | 1.88± | 2.00 ± 0.15[✕] |
| Example | 15 | 1.99 ± 0.17 | 2.04 ± 0.11 | 2.17± | 2.06 ± 0.12 | 2.01± | 2.13 ± 0.23 |
| Example | 15 | 2.07 ± 0.11 | 2.13 ± 0.28[✕] | 2.14 ± 0.13 | 2.02 ± 0.10 | 2.01± | 2.15 ± 0.13 |

Note:
[#] compared with blank group, $p < 0.05$,
[##] compared with blank group, $p < 0.01$,
[✕]compared with model group, $p < 0.05$,
[✕✕] compared with model group, $p < 0.05$.

TABLE 9

Thermalgia threshold of rats

| Groups | The number of cases | Pain threshold 3 h | Pain threshold 6 h | Pain threshold 24 h | Pain threshold 7 d | Pain threshold 9 d | Pain threshold 11 d |
|---|---|---|---|---|---|---|---|
| blank group | 15 | 15.44 ± 2.2 | 14.87 ± 1.35 | 15.43 ± 2.60 | 14.85 ± 3.61 | 15.84 ± 3.33 | 14.17 ± 3.53 |
| model group | 15 | 15.56 ± 3.42 | 18.81 ± 2.38[#] | 16.68 ± 2.21[#] | 17.79 ± 1.83[#] | 16.12 ± 3.13 | 16.80 ± 4.13[#] |
| Example | 15 | 15.12 ± 4.17 | 16.22 ± 3.18[✕] | 15.22 ± 1.13[✕] | 17.06 ± 2.13 | 15.08 ± 3.08[✕] | 16.05 ± 3.05 |
| Example | 15 | 15.78 ± 3.23 | 16.12 ± 3.22 | 15.58 ± 1.23 | 16.96 ± 3.61 | 13.22 ± 2.45[✕] | 12.54 ± 2.23[✕] |
| Example | 15 | 15.25 ± 1.37 | 15.45 ± 1.31 | 15.99 ± 3.46 | 15.01 ± 3.24 | 14.08 ± 2.34[✕] | 13.07 ± 1.40[✕] |
| Example | 15 | 15.22 ± 3.56 | 14.99 ± 2.43[✕] | 14.92 ± 2.34[✕] | 14.04 ± 2.14[✕] | 16.01 ± 1.21 | 14.44 ± 2.13[✕] |

TABLE 9-continued

Thermalgia threshold of rats

| Groups | The number of cases | Pain threshold 3 h | Pain threshold 6 h | Pain threshold 24 h | Pain threshold 7 d | Pain threshold 9 d | Pain threshold 11 d |
|---|---|---|---|---|---|---|---|
| Example | 15 | 15.09 ± 3.27 | 16.23 ± 2.34 | 15.22 ± 3.14 | 15.76 ± 3.34 | 15.23 ± 3.16✕ | 16.05 ± 3.46 |
| Example | 15 | 15.33 ± 2.12 | 16.50 ± 3.06✕ | 15.25 ± 3.18 | 15.25 ± 3.18 | 15.28 ± 1.08✕ | 15.15 ± 2.11✕ |

Note:
[#] compared with blank group, $p < 0.05$,
[##] compared with blank group, $p < 0.01$,
[✕] compared with model group, $p < 0.05$,
[✕·✕·] compared with model group, $p < 0.05$.

TABLE 10

Content of pain related factors NK-1R, COX-2 in different groups

| Groups | The number of cases | Content of P substance (pg/mL) | NK-1R | COX-2 |
|---|---|---|---|---|
| blank group | 15 | 178.913 ± 22.694 | 0.0222 ± 0.00073 | 0.0146 ± 0.00101 |
| model group | 15 | 458.778 ± 114.340[#] | 0.0648 ± 0.00782[#] | 0.0384 ± 0.00248[#] |
| Example 1 | 15 | 325.511 ± 43.059✕ | 0.0339 ± 0.00065✕ | 0.0249 ± 0.00182✕ |
| Example 2 | 15 | 325.511 ± 7.78✕ | 0.0334 ± 0.00187✕ | 0.0233 ± 0.00079✕ |
| Example 3 | 15 | 277.167 ± 24.356✕ | 0.0397 ± 0.00124✕ | 0.0245 ± 0.00064✕ |
| Example 4 | 15 | 310.511 ± 13.975✕ | 0.0338 ± 0.00087✕ | 0.0210 ± 0.00389✕ |
| Example 6 | 15 | 299..511 ± 33.456 | 0.0339 ± 0.00357✕ | 0.0240 ± 0.0024✕ |
| Example 7 | 15 | 343.840 ± 84.959 | 0.0452 ± 0.00113✕ | 0.0303 ± 0.00184✕ |

Note:
[#] compared with blank group, $p < 0.05$,
[##] compared with blank group, $p < 0.01$,
[✕] compared with model group, $p < 0.05$,
[✕✕] compared with model group, $p < 0.05$.

The above experimental results demonstrate that all of the compositions of cinnamon bark oil and nutmeg oil in different proportion have obvious effect on relieving chronic pain.

The description above is only the preferred embodiments of the present invention. It should be noted that, those having ordinary skill in the area can make several modifications and polishments without departing from the principles of the present invention, and these modifications and polishments should be regarded as falling within the protection scope of the present invention.

The invention claimed is:

1. A preparation method of a traditional Chinese medicine composition for relieving chronic pain, wherein the traditional Chinese medicine composition consists of cinnamon bark oil and nutmeg oil, the mass ratio of cinnamon bark oil to nutmeg oil is (1-10):(1-10), the preparation method includes the following steps:

subjecting cinnamon bark to water vapor distillation for the first extraction, yielding cinnamon bark oil;

subjecting nutmeg to water vapor distillation for the second extraction, yielding nutmeg oil; and mixing the cinnamon bark oil and the nutmeg oil, yielding the traditional Chinese medicine composition.

2. The preparation method according to claim 1, wherein the first extraction is: pulverizing cinnamon bark and then soaking it into water, then extracting by water vapor distillation; the time for extraction by distillation is 0.5-6 h;

the second extraction is: pulverizing nutmeg and then soaking it into water, then extracting by water vapor distillation; the time for extraction by distillation is 1-12 h.

* * * * *